United States Patent [19]

Bessiere et al.

[11] Patent Number: 5,015,957

[45] Date of Patent: May 14, 1991

[54] AMPEROMETRIC METHOD FOR MEASURING ACIDITY

[75] Inventors: Jacques Bessiere, Gondizeville; Michel Perdicakis, Nancy, both of France

[73] Assignee: Electricite de France (Service National), Paris, France

[21] Appl. No.: 375,578

[22] Filed: Jul. 5, 1989

[30] Foreign Application Priority Data

Jul. 6, 1988 [FR] France ................... 88 09161

[51] Int. Cl.$^5$ ............................................. G01N 27/02
[52] U.S. Cl. ..................................... 324/438; 204/405; 324/446
[58] Field of Search ............... 324/438, 439, 446, 425; 204/1 T, 405, 400, 406

[56] References Cited

U.S. PATENT DOCUMENTS 3,647,641  3/1962  Grubb ................... 204/1 T
4,406,751  9/1983  Blass et al. .............. 204/1 T

FOREIGN PATENT DOCUMENTS 2013378  3/1970  Fed. Rep. of Germany .
WO88/00342  1/1988  PCT Int'l Appl. .

OTHER PUBLICATIONS

MacFarlane et al., "Thin-Ring Ultra-Microelectrodes", J. Electroanal. Chem., 185 (12/1985), pp. 197-202.

Wang et al., "Anodic Stripping Voltammetry at Ultramicroelectrodes for Metal Speciation Studies in Aqueous Solutions of Low Ionic Strength", J. Electroanal. Chem., 246 (12/1988), pp. 297-305.

Primary Examiner—Kenneth Wieder
Assistant Examiner—Robert W. Mueller
Attorney, Agent, or Firm—Blakely, Sokoloff, Taylor & Zafman

[57] ABSTRACT

An amperometric method for the direct measurement of acidity in a medium which contains at least one ester of an acid containing oxygen, and whose dielectric constant is lower than 30. The method provides for maintaining a constant voltage between an ultramicroelectrode and a counterelectrode and measuring the current therebetween as an increasing quantity of diphenylphosphoric acid is added to the medium via a microburette. The measured current being indicative of the acidity of the medium under test. A predetermined curve is provided which represents the relationship between the acidity of the medium and the current measured by the system.

20 Claims, 1 Drawing Sheet

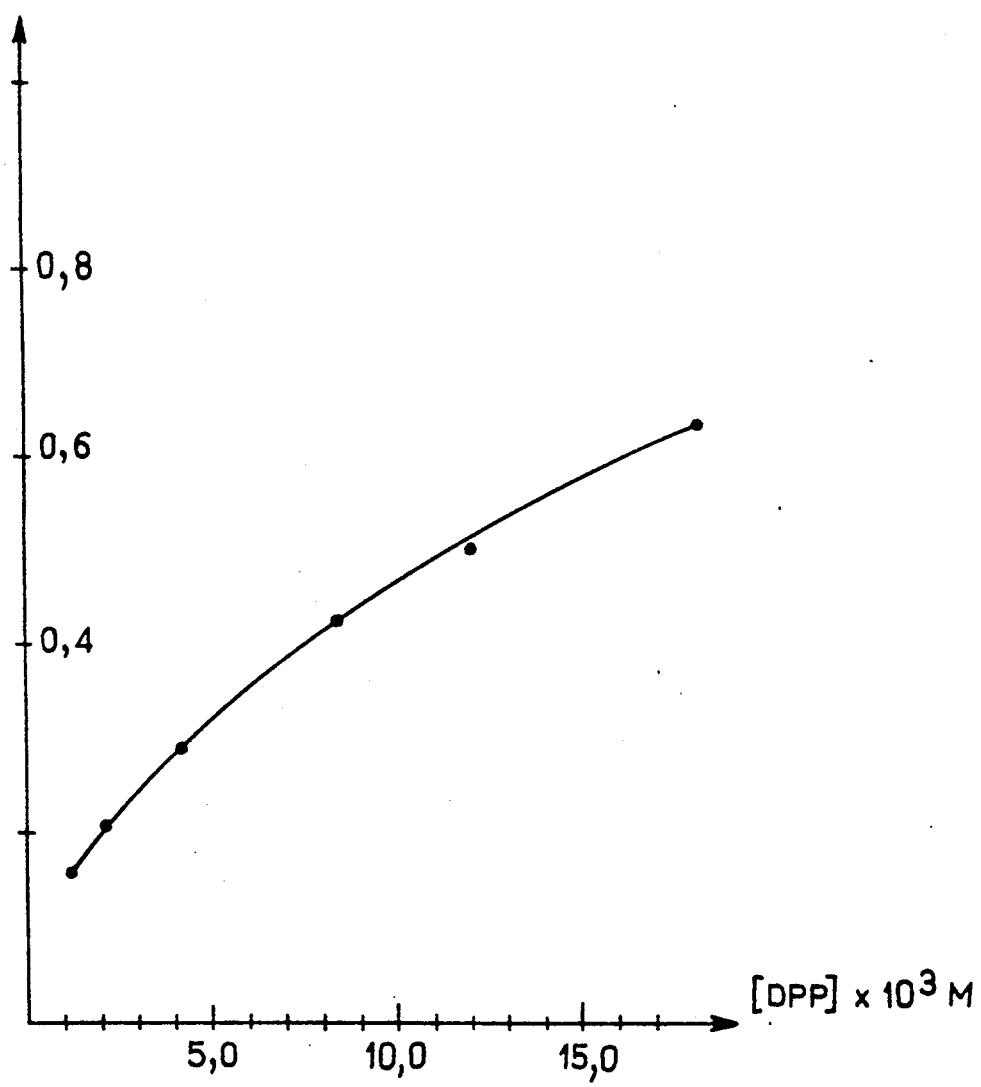

AMPEROMETRIC METHOD FOR MEASURING ACIDITY

The present invention relates to an amperometric method for measuring the concentration of a dissolved species.

Its subject is more particularly a method for measuring acidity in a medium which is a very poor conductor of electricity.

By way of indication, a very poor conductor means a medium whose conductivity is lower than approximately $10^{-4}$, in general than $10^{-5}$ ohm$^{-1}$ cm$^{-1}$.

Many organic fluids are employed in the various fields of industrial activity. Decomposition of these organic fluids frequently gives rise to acidic compounds, be this decomposition the result of an oxidation, a thermolysis or a hydrolysis.

More particularly, esters of inorganic acids or of organic acids and more particularly esters of phosphoric acids have been the subject of considerable development as a constituent or component of synthetic lubricating oil, of heat transfer fluid or as an additive in actuating fluids.

When they decompose, these esters frequently give rise to acids, for example by hydrolysis or by thermolytic or oxidizing scission. They can also give acids by the oxidation of the alcohol to an aldehyde and then to an acid.

The acidity released is extremely harmful, alters the lubricating properties and presents corrosion hazards to the metal parts with which the fluid comes into contact. This has the twin disadvantage of appreciably altering the composition of the fluid and, furthermore, of reducing the strength of the containers in which the said fluids are present.

It is therefore important to monitor the acidity level of these fluids very closely, in order to take all the measures which might be found necessary, such as, for example, introducing an esterification agent, removing the acid by passing through a bed of an acid-absorbent (basic or resin support, etc.) or replacing the fluid.

One of the most widely employed methods for doing this is, of course, the sampling and an acidometric determination of the said fluid. However, this method cannot always be employed, firstly because the response time may be too long and, secondly, because the sampling may be difficult, dangerous, costly or even impossible; this is the case especially with fluids of this type which are employed in the hot areas of the nuclear industry.

To solve this problem, and since pH measurement is virtually impossible using normal methods in nonconductive media, attention has turned towards indirect, or even very rudimentary measurement methods.

These methods are essentially based on the corrosiveness of the medium, either measuring the potential difference between two electrodes of different metals, or using a fuse, the failure of the fuse indicating that the degree of acidity and of decomposition of the fluid has reached a critical level.

Another device of this type is described in the French Patent Application published under no. 2,527,775. This device is a corrodible probe through which a direct or alternating electrical current can be passed; the measurement of the resistance or of the impedance of the corroded probe constitutes the indirect measurement of the acidity of the medium.

In actual fact, this indirect measurement remains very approximate, because it cannot take into account kinetic effects, which are not always directly related to the acid concentration. It is appropriate to emphasise here that, each time the acidity reaches a critical level, an operator needs to intervene to change the measurement or probe system, the fuses and the probes being consumable fuses and probes in all cases. The person skilled in the art is well aware of the disadvantage of such methods in the hot areas of the nuclear industry.

This is why one of the objectives of the present invention is to provide a method for measuring the decomposition of the fluids of the type described above, which is direct.

Another objective of the present invention is to provide a method of the above type which measures the acidity released by the decomposition of the fluids of the above type.

Another objective of the present invention is to provide a method which does not require frequent interventions at the site of measurement.

Another objective of the present invention is to provide a method of the above type which does not require the modification of the fluids on the occasion of or due to additions of titration reactants.

Another objective of the present invention is to provide a device which is capable of employing a method of the above type.

These objectives and others which will become apparent later are achieved by means of an amperometric method for measuring acidity in a very poorly conductive medium, characterized in that an assembly comprising a measuring ultramicroelectrode and a counterelectrode is employed. An ultramicroelectrode should be understood to mean a microelectrode whose surface area does not exceed 8000 square micrometers.

One of the major limitations of the methods employed hitherto and making use of potentiometric or voltaperometric measurements is the need to employ a reference electrode. Such an electrode is fragile and its lifespan is not compatible with use in hot areas. Furthermore, it runs the risk of contaminating, for example by diffusion, the medium whose acidity is to be measured. This contamination increases with time which is not insignificant by the end of a week, it becomes significant by the end of a month and considerable by the end of one to several quarters. This problem of contamination is not only linked with the use of fluids which operate in hot areas; it is linked with all measurements of the medium which must not be contaminated by reactants linked with the use of the measurement. In addition, this contamination is correlated with a loss in efficiency of the reference electrode, which must then be changed quite quickly, which is contrary to one of the objectives of the invention.

Another of the major limitations of amperometric methods is that until now they demanded the presence of a supporting electrolyte, especially when the medium in which the measurement is carried out is a poor conductor of electricity.

To be sure, papers such as those published in J. Electroanal. Chem. 168 (1984) 299-312 and J. Electroanal. Chem. 220 (1987) 31-40, under the respective titles "Electrochemistry in Organic Solvents without Supporting Electrolyte Using Platinum Microelectrodes" and "Voltammetric Measurements with Microelectrodes in Low-Conductivity systems", show the possibility of carrying out electrochemical mechanistic studies in the absence of a supporting electrolyte when neutral molecules (ferrocene) are involved, and consequently when an ultramicroelectrode is employed in combination with a reference electrode and a counterelectrode.

In addition, a problem which is specific to oxygen-containing esters and more particularly phosphoric esters, is that any measurement of an amperometric or polarographic type was considered impossible by specialists in this subject (cf. V. Gutmann's reference work, Coordination Chemistry in Non-Aqueous Solutions, published by Springer-Verlag, Vienna, N.Y. 1968, page 151), this being even in the presence of a supporting electrolyte.

Thus, in the course of the investigations which led to the present invention it was shown that, in the case of a given potential difference between an ultramicroelectrode and a counterelectrode, and not between an ultramicroelectrode and a reference electrode, that there was a simple and reproducible correlation between the current flowing between the counterelectrode and the ultramicroelectrode, on the one hand, and the acidity of the medium, on the other hand, and that it was thus possible to measure this acidity by amperometry.

The surface area of the ultramicroelectrode, which is determined by the diameter of the wire from which it is manufactured and which corresponds substantially to the surface area of its cross-section plays a very major part in the measurement.

According to the present invention, the surface area must be correspondingly smaller, the lower the dielectric constant of the medium in which the acidity is to be measured. Thus, while it is possible to perform measurements with an ultramicroelectrode 100 $\mu$m in diameter in the case of dielectric constants of the order of 80, it is necessary to go down to values in the region of 50 $\mu$m in the case of dielectric constants below 40; diameters corresponding to 10 $\mu$m make it possible to go down to dielectric constants of the order of 5. Advantageously, it must not be greater than 50 $\mu$m in the case of dielectric constants higher than 30, than 10 $\mu$m in the case of dielectric constants of between 10 and 15, and of the order of 1 $\mu$m in the case of dielectric constants of between 5 and 10. However, it is possible to perform less accurate measurements with a 1 -$\mu$m electrode when the dielectric constant is lower than 5 (the zeros shown above are not significant digits).

For a better measurement it is preferable to have ultramicroelectrodes whose diameter is as low as possible. Manufacturing methods alone constitute a limiting factor, as well as the measurements of current detection, which must then have a sensitivity better than a nanoampere. Thus, a compromise must be found between the sensitivity of the devices measuring the current flowing between the two electrodes, which is limited, and, on the other hand, the cross-section of the wires used to manufacture the ultramicroelectrodes.

These ultramicroelectrodes are generally made of a wire of substantially cylindrical shape, embedded in a sheath which is generally of glass, and whose end is polished so that the cross-section of the metal wire constitutes the microelectrode. Thus, the ultramicroelectrode consists of a substantially disc-shaped surface area whose diameter is very small.

The choice of the potential difference applied between an ultramicroelectrode and a counterelectrode depends on the size and the nature of the ultramicroelectrode and on the nature of the counterelectrode.

The potential difference applied is preferably chosen so that the potential taken by the ultramicroelectrode lies in the potential region corresponding to the diffusion limit current of the chemical species whose concentration is to be measured. If it is not possible to reach this diffusion limit current, then, according to the present invention, the surface area of the ultramicroelectrode should be reduced.

This method is suitable for measuring an acidity whose upper limit is $10^{-1}$N, advantageously $10^{-2}$N and the lower limit $10^{-5}$, advantageously $10^{-4}$ and preferably $10^{-3}$N; the lower limits are, furthermore, limitations which are not related to electrochemical factors according to the present invention, but are related to the devices responsible for imposing the potential between the two electrodes and measuring the current flowing in the cell.

By way of indication, in the case of an acidity measurement with a zinc counterelectrode in a phosphoric ester, a potential of the order of 1 volt is perfectly suitable.

By way of indication, the acidity measurement can be determined for all the acids whose pK values do not exceed 11, preferably 7. These values are only rough, since these values are values given for an acidity measured in water and since the actual acidities vary according to the medium.

During the study which led to the present invention it was demonstrated that, in order to avoid the interference phenomena originating from the counterelectrode, it was preferable for the latter to have a surface area much greater than that of the ultramicroelectrode.

The ratio of the areas of these two electrodes is preferably at least 10, advantageously 100 (one significant digit). In difficult cases, when a ratio of 10 is found insufficient, the person skilled in the art will increase this ratio until the time when a further increase in the ratio no longer changes the results.

As, in fact, there is no significant upper limit to this ratio and as this ratio depends on the medium and on the nature of the counterelectrode and the species in solution, ratios which are much higher than that of 10 are generally employed for safety and ratios which are higher than 1,000 (or even 10,000) can be indicated as satisfactory. When such a system is installed in a hot region or when it is intended to operate for a long time without being changed, in the case of soluble anodes, it is appropriate to provide not only a surface area, but also a mass and a geometrical shape which permit corrosion or electrosolubilization, without there being a significant change in the ratio of the surface areas specified above and so that this latter ratio remains within the limits which give good results throughout the period of operation.

When the counterelectrode is an anode, it is advantageous for the anode to be made of a nonpolarizable metal such as, for example, platinum, or else that the anode be made of an element which is electrosoluble in the conditions of the experiment. Although the quantities dissolved are negligible, the electrosoluble element is preferably harmless to the medium. Zinc is perfectly suitable for measurement in phosphoric ester media. In general, counterelectrodes of very large surface area relative to the surface area of the ultramicroelectrode and made of electrosoluble metal, that is to say giving rise to an anodic oxidation reaction, and whose oxidation product is soluble in the medium in the experimental conditions, give particularly satisfactory and particularly well-reproducible results.

The present method of measurement gives particularly satisfactory results and is well adapted to the measurement of the acidity released in organic or inorganic aprotic esters (preferably of oxygen-containing acids) whose dielectric constant is lower than 30, this acidity being released by the decomposition of the said esters or of their solvents or else of their solutes. The said esters may be diluted in a proportion varying from 1/10th to 10 in various very poorly conductive diluents; the said esters preferably represent at least one third of the fluid by volume. More specifically, the method according to the invention is suitable in the case of phosphoric ester mixtures such as those of various tertbutylphenyl and phenyl phosphates such as that sold under the trademark Fyrquel VPF.

The ultramicroelectrode may be made of various metals or alloys or conductive materials, but those preferably employed are ones which, like gold, platinum and their group, exhibit a low hydrogen overvoltage; stainless steel is in a place of its own and also gives excellent results.

The most appropriate inorganic acid esters are oxygen-containing esters.

The invention is particularly well-suited for the measurement of the decomposition of phosphoric esters corresponding to the general formula:

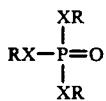

in which:

X=O or a single bond, the groups R are identical or different and are chosen from alkyl, aryl, aralkyl and alkaryl radicals containing from 1 to 20 atoms, preferably from 1 to 10, of carbon. The radicals R themselves may have various functional groups which correspond to specific uses of the said functional fluids.

In fact, the acidity of a diesterified phosphoric acid corresponds to that of the first functional group of the said acid. This acidity is easily measurable according to the method of the present invention. It is also possible to envisage measuring in this way the decomposition of phosphonic or phosphinic esters, or even of trialkylphosphine oxide, alkyl having here the meaning of the group R. The acidity of carboxylic acids, or even of phenols, can also be determined according to this method, and this is of interest for measuring the decomposition of fatty substances of plant or animal origin.

The measuring method according to the present invention must not be limited only to the nuclear utilizations or to the case where access to the fluid is difficult. The simplicity of the measurement, its reliability and the accessibility of the necessary hardware makes the method accessible for any use where fluids of the type described above are employed. Thus, it is possible to envisage a measurement of the degree of decomposition of neutral phosphorus-containing extractants, exemplified by trioctylphosphine oxide and tributyl phosphate.

If need be, a reference electrode may be employed, when the identification of an interfering species or phenomenon requires it. However, the measurement will need to remain exceptional and to be carried out only as a temporary measure.

Another objective of the present invention is to provide a device for making use of the above method. The objective is attained by an amperometric device for measuring chemical species in solution in a very poorly conductive medium, characterized in that it comprises an ultramicroelectrode, a counterelectrode, a stabilized voltage supply and a means for measuring the current between the said ultramicroelectrode and the said counterelectrode and in that the ratio between the surface area of the counterelectrode and the ultramicroelectrode is at least equal to 10.

A preferred device for making use of the invention is a device which consists of a counterelectrode whose surface area is 10,000 times greater than that of the electrode described hereinafter and an ultramicroelectrode in which the diameter of the effective disc is smaller than 100 microns and preferably smaller than 10 microns. The ultramicroelectrodes marketed, such as those sold by the company Tacussel, are suitable for this use.

These electrodes are connected to a voltage stabilizer fitted with an amperometric measurement system, such as that marketed by the company P.A.R. (Princeton Applied Research) under the name PAR 174A.

The measurement method chosen (for example impulsive or superimposed sinusoidal) does not alter the essence of the invention and contributes these particular specific features to the method according to the invention.

BRIEF DESCRIPTION OF THE DRAWING

The single FIGURE shows a graph of the measured current vs. the concentration during the addition of increasing quantities of acid.

The example which follows, without any limitation being implied, and the single FIGURE illustrating the invention will enable the person skilled in the art to make a better assessment of its advantage.

Measurement of acidity in the lubricant Fyrquel VPF

Equipment employed:

P.A.R.174A polarographic analyser

Kipp and Zonen BD90 X-Y recorder

Metrohm electrochemical cell (measurement and universal titration vessel 6.570X.XXX; lid 6.1414.010; cell with a thermostatic jacket 6.1418.150) thermostated at 49° C. and placed in a solid-walled Faraday cage;

Tacussel Znl2 zinc counterelectrode

Tacussel MEPT 10 platinum ultramicroelectrode, $\phi 10\ \mu m$

Gilmont 0.2-ml microburette

Fyrquel VPF lubricant sold by Stauffer $1.01 \times 10^{-1}$M solution of diphenylphosphoric acid in Fyrquel VPF.

The "reference electrode" and "auxiliary" cards of the polarograph are short-circuited and connected to the zinc electrode.

The working electrode is connected to the platinum ultramicroelectrode.

The voltage imposed between the ultramicroelectrode and the counterelectrode is 1.00 V.

As shown in FIG. 1, the results/are collated as the curve of the single FIGURE, which is obtained by measuring the current (I in nA) passing through the electrodes during the addition (using the microburette) of increasing quantities of diphenylphosphoric acid (in solution in Fyrquel VPF) to an initial volume of 10 ml of lubricant placed in the electrochemical cell.

In this case, the solution was at rest during the measurement and was not degassed. If the solution is stirred, similar results are obtained, but the measured current values are slightly higher. Degassing of the solution is reflected in a slight decrease in the measured currents, of the order of 10%.

We claim:

1. An amperometric method for the direct measurement of acidity in a medium which contains at least one ester of an acid containing oxygen, and whose dielectric constant is lower than 30, comprising the steps of:
   (a) fixing a given voltage between a measuring ultramicroelectrode and a counterelectrode, which together with said medium form an electrochemical cell, the ratio between the surface area of the counterelectrode and the ultramicroelectrode being at least equal to 10;
   (b) measuring the current between said ultramicroelectrode and said counterelectrode; and
   (c) correlating the current measured in step (b) to the acidity of the medium by use of a curve which represents the relationship between the currents passing through the electrodes during the addition of increasing quantities of diphenylphosphoric acid via a microbarette to an initial volume of 10 ml of said medium.

2. Method according to claim 1, characterized in that the ratio between the surface area of the counterelectrode and the ultramicroelectrode is at least equal to 100.

3. Method according to claim 1, characterized in that said ultramicroelectrode is substantially in the shape of a disc whose diameter is less than 50 micrometers.

4. Method according to any of claims 1, 2, or 3, characterized in that said ultramicroelectrode is made of platinum or gold.

5. Method according to claim 4, characterized in that said counterelectrode is made of the group consisting of electrosoluble elements and their alloys, and of the metals of the platinum group.

6. Method according to claim 5, characterized in that said oxygen-containing ester is an ester of phosphoric acid.

7. Method according to claim 5, characterized in that said ester is a phosphoric ester of the general formula:

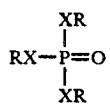

in which:
X = O or a single bond,
the groups R are identical or different and are chosen from alkyl, aryl, aralkyl and alkaryl radicals containing from 1 to 20 atoms, preferably from 1 to 10, of carbon.

8. Method according to claim 7 in which said medium is the lubricant Fyrquel VPS.

9. Method according to claim 4, characterized in that said oxygen-containing ester is an ester of phosphoric acid.

10. Method according to any of claims 1, 2 or 3, characterized in that said ultramicroelectrode is made of stainless steel.

11. Method according to claim 10, characterized in that said counterelectrode is made of the group consisting of electrosoluble elements and their alloys, and of the metals of the platinum group.

12. Method according to claim 11, characterized in that said oxygen-containing ester is an ester of phosphoric acid.

13. Method according to claim 11, characterized in that said ester is a phosphoric ester of the general formula:

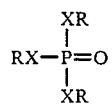

in which:
X = O or a single bond,
the groups R are identical or different and are chosen from alkyl, aryl, aralkyl and alkaryl radicals containing from 1 to 20 atoms, preferably from 1 to 10, of carbon.

14. Method according to claim 13 in which said medium is the lubricant Fyrquel VPS.

15. Method according to claim 10, characterized in that said oxygen-containing ester is an ester of phosphoric acid.

16. Method according to any of claims 1, 2 or 3, characterized in that said counterelectrode is made of the group consisting of electrosoluble elements and their alloys, and of the metals of the platinum group.

17. Method according to claim 16, characterized in that said oxygen-containing ester is an ester of phosphoric acid.

18. Method according to claim 16, characterized in that said ester is a phosphoric ester of the general formula:

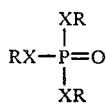

in which:
X = O or a single bond,
the groups R are identical or different and are chosen from alkyl, aryl, aralkyl and alkaryl radicals containing from 1 to 20 atoms, preferably from 1 to 10, of carbon.

19. Method according to claim 10 in which said medium is the lubricant Fyrquel VPS.

20. Method according to any of claims 1, 2 or 3, characterized in that said oxygen-containing ester is an ester of phosphoric acid.

* * * * *